United States Patent [19]

Razgulov et al.

[11] 4,202,479
[45] May 13, 1980

[54] SURGICAL INSTRUMENT FOR SUTURING TUBULAR ORGANS WITH U-SHAPED STAPLES

[76] Inventors: Mikhail M. Razgulov; Tamara A. Razgulova, both of ulitsa Mashinostroitelei, 32, kv. 80, Podolsk Moskovskoi oblasti, U.S.S.R.

[21] Appl. No.: 11,697

[22] Filed: Feb. 12, 1979

[51] Int. Cl.² .............................................. A61B 17/12
[52] U.S. Cl. ......................................... 227/8; 227/19; 227/111
[58] Field of Search ............. 128/334 R; 227/19, 120, 227/8, 110, 111, 155

[56] References Cited
U.S. PATENT DOCUMENTS 3,790,057  2/1974  Razgulov et al. ..................... 227/19

*Primary Examiner*—Paul A. Bell
*Attorney, Agent, or Firm*—Steinberg & Blake

[57] ABSTRACT

The instrument is characterized in that provision is made therein for a means preventing the staple semibushes from being disjoined in the course of operation and fixing the position of the center of the hole of said staple semibushses with respect to the position of the center of the hole of the supporting semibushes so as to provide a uniform suturing of the tubular organ, whereas the magazines are so mounted as to be replaced after the operation, for which purpose the magazine and staple semirings have through curvilinear grooves and are detachable with respect to said staple semibushes, the outer walls of the latter having recesses for said magazines to reload, said recesses being arranged along the radius coinciding with the radius of the radial slots in said staple semibushes. In addition, provision is made in the instrument for an automatic restrictor of synchronous radial movement of said magazines and said ejectors towards the center.

7 Claims, 32 Drawing Figures

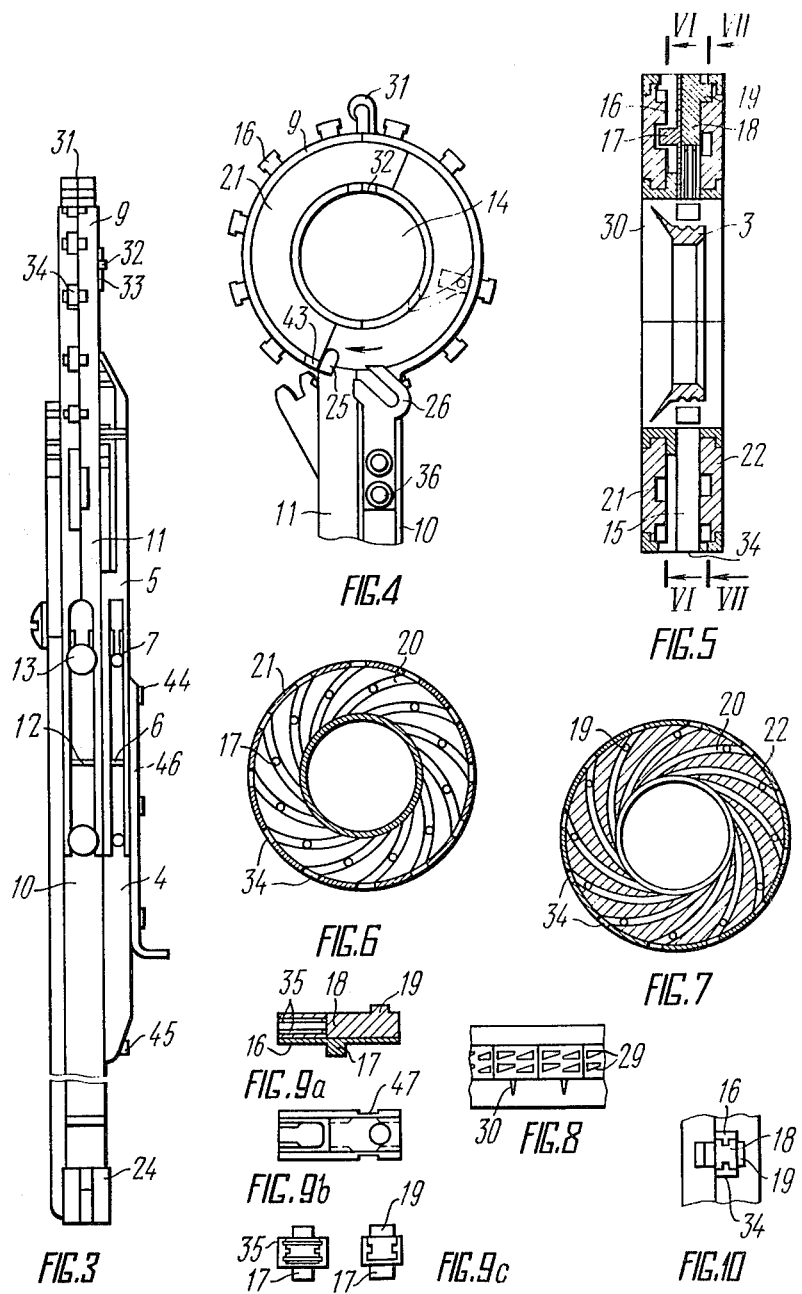

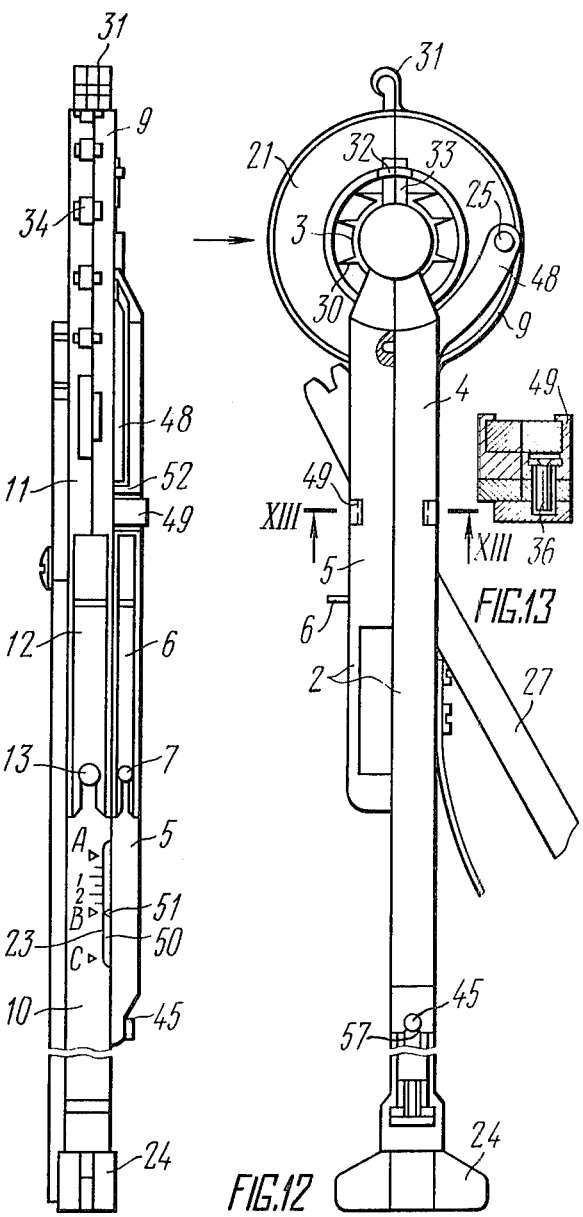

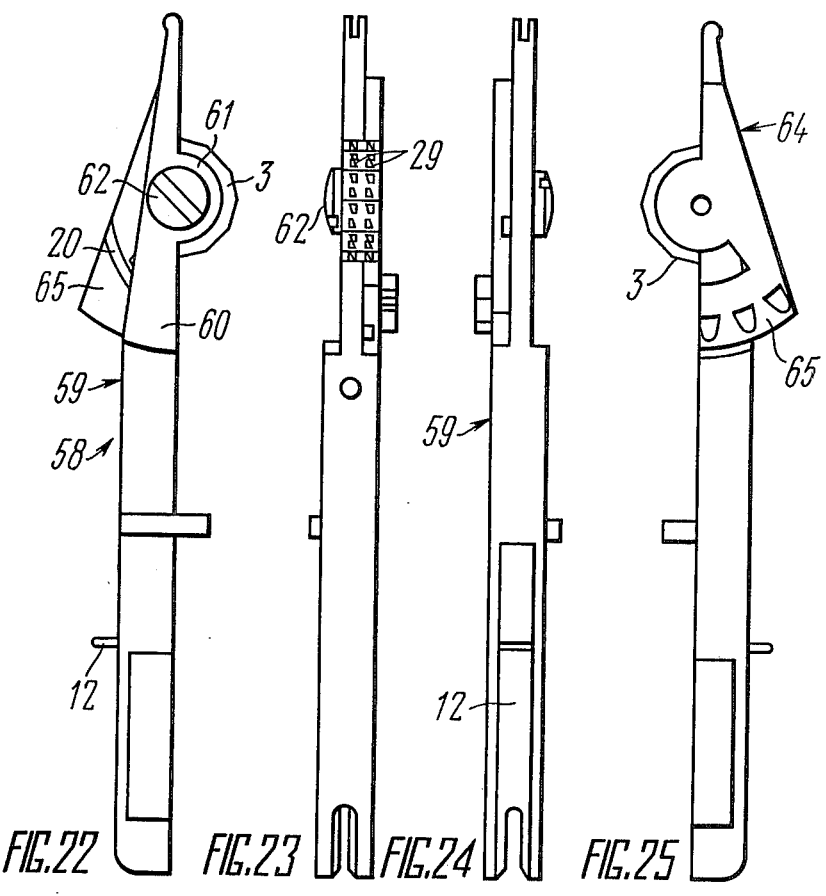

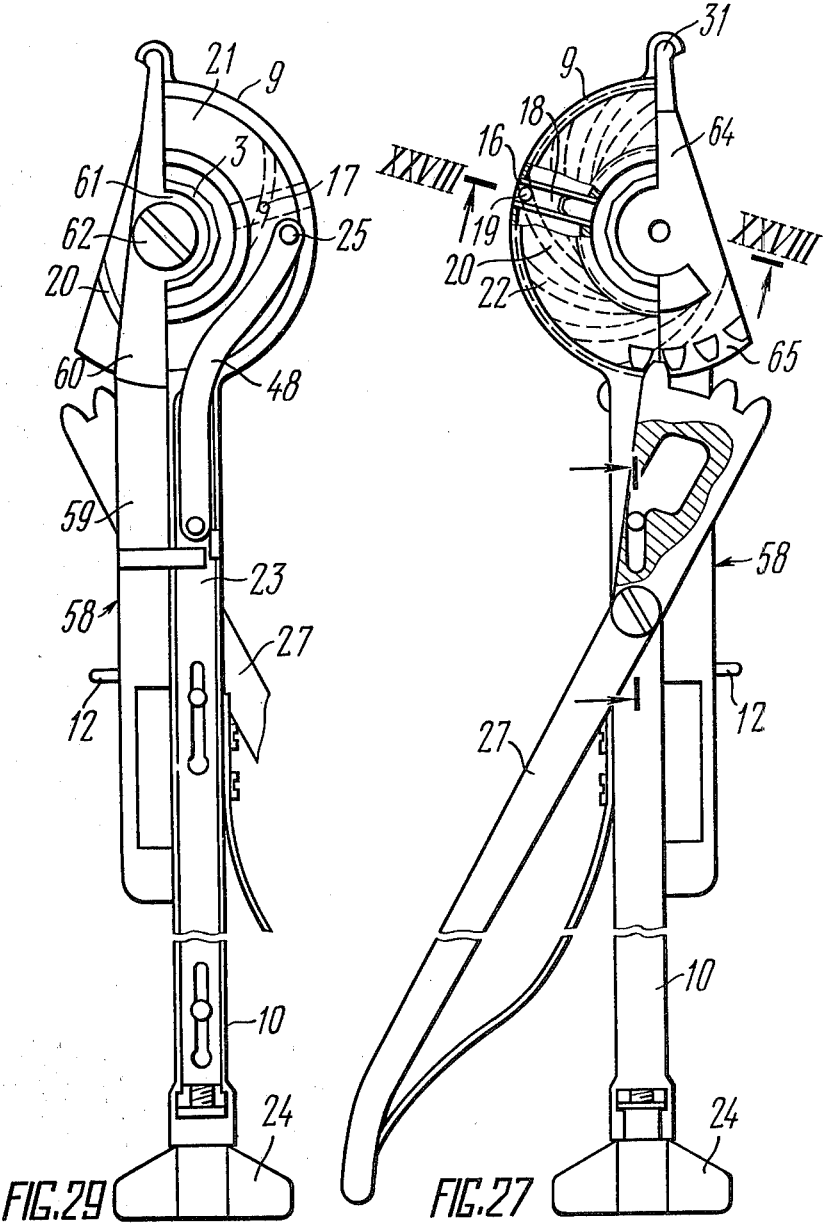

SURGICAL INSTRUMENT FOR SUTURING TUBULAR ORGANS WITH U-SHAPED STAPLES

The present invention relates to medical equipment, namely, to surgical instruments for suturing tubular organs with U-shaped staples, applicable for suturing various blood vessels (such as veins, arteries, the aorta, etc.), as well as some other tubular organs.

One prior-art surgical instrument for suturing blood vessels with U-shaped staples is known in to use currently (cf. USSR Inventor's Certificate No. 345,712 cl. A 61b, 17/II/.

The known surgical instrument consists of two members, viz., the supporting and the staple ones.

The supporting member comprises two supporting semibushes of which one is held to the supporting body and the other, to the supporting strip. The supporting strip is locked in position with respect to said supporting body. When brought together the two supporting semibushes establish a cylinder-shaped supporting bush whose bore is adapted for the tubular organ being sutured to accommodate.

The staple member comprises two staple semibushes of which one is held to the staple body and the other, to the staple strip which is locked in position with respect to said staple body. When brought together the staple body and the staple strip define the staple member of the instrument, whereas the staple semibushes also form in this position a cylinder-shaped staple bush whose bore is adapted for the tubular organ being sutured to accommodate.

Depressions for staple to bend are provided on the outer cylindrical surface of the supporting semibushes. The staple semibushes adapted to accommodate staple magazines containing a single row of staples, and staple ejectors located inside the magazines, are provided with radial slots arranged opposite the respective depressions provided in the supporting semibushes. Said slots accommodate movably mounted staple magazines and ejectors, both of them having pivots arranged in curvilinear grooves made in the staple and magazine semirings and adapted to get in movable engagement therewith.

The staple member of the instrument is locked in position with respect to the supporting member thereof, the staple semibushes externally embracing the supporting semibushes so that an annular gap is defined therebetween for the walls of the tubular organ being sutured to accommodate.

The surgical instrument under discussion has the mechanical actuator for the magazine semirings to traverse, made as a strip traversable with respect to the staple body. One of the strip ends is threaded to engage the sliding nut, the other end being adapted to interact with the lug made fast on the magazine semiring of the staple semibush which, in turn, is held to the stable body.

The surgical instrument in question has the mechanical actuator for the staple semirings to traverse, made as an actuating lever involutely coupled with the staple semirings.

The supporting semibushes and the mating staple semibushes are so selected as to suit the diameter of the tubular organ to be sutured, i.e., the outside diameter of the brought-together supporting semibushes should be nearly equal to the inside diameter of the tubular organ.

One of the ends of the tubular organ being sutured is embraced from outside by the supporting semibushes. The vessel end is put on the spikes on the side of the tunica extima, whereupon the other vessel end is put on the same spikes on the side of the tunica intima. Then the staple body is introduced into the wound, next the staple strip, both of them being fixed in position with respect to each other and to the supporting member of the instrument. Thus, the instrument is completely assembled on the tubular organ being sutured. Thereupon the suturing gap is adjusted by rotating the sliding nut, and the actuating lever is pressed to traverse the ejectors which expell the staples from the staple slots to pierce the walls of the tubular organs being sutured and, upon thrusting against the depressions in the supporting bush, get bent into the shape of the letter B, thus uniting the ends of the tubular organs being sutured.

Next the instrument is removed from the thus-sutured tubular organ in the reverse sequence.

The known instrument enables suturing of tubular organs having a total thickness of two walls being stitched up within 0.2 to 3 mm, including aterosclerotic blood vessels with vascular transplants. The suturing procedure takes 1 to 2 minutes to occur.

However, the above-discussed instrument is capable of applying only a single-row staple suture whose tightness, especially in the case of suturing the aorta, is far from being quite adequate. Such a vascular anastomosis needs an auxiliary hemostatic suture to be applied. Apart from that the process of loading the staple semibushes with U-shaped staples is a tedious one taking much time to carry out. In addition, the staple semibushes are liable to bring apart at the moment of setting the suturing gap and in the course of suturing, which results in the magazine and staple semirings getting jammed. Such being the case the instrument cannot sometimes be removed from the vessel. The supporting semibushes tend to considerable displace at the moment of suturing under the effect of lateral thrust which might result at best in an inadequately bent staples along the periphery of the suture, and at worst in that the staple legs fail to catch their respective depressions and the suture proves to be ineffective. The mode of holding the staple and supporting strips to the respective bodies, as well as that of fixing the supporting member of the instrument to the staple member thereof fails to provide for an adequate robustness to the entire construction of the instrument. At last washing and cleaning of the staple semibushes offer some difficulties, while dismantling of said unit is too complicated and needs additional tools to be applied.

It is a primary object of the present invention to provide such a surgical instrument for suturing tubular organs with U-shaped staples that features the constructional arrangement of individual units thereof which would be capable of positively locking the staple and supporting strips to the respective bodies and of imparting an adequate robustness to the entire construction.

It is another object of the present invention to provide a high quality tightness of the tubular organ being sutured, the thoracic aorta inclusive.

It is one more object of the present invention to provide complete washing and sterilization of the surgical instrument disclosed herein.

The essence of the invention resides in the fact that in a surgical instrument for suturing tubular organs with U-shaped staples, comprising two supporting semibushes of which one is held to a supporting body and the other, to a supporting strip held in position with respect to said body, both of said semibushes being adapted, when brought together, to establish a supporting member of the instrument having a cylindrical bore for the tubular organ to pass; two staple semibushes adapted to accommodate magazines which contain a single row of staples, and staple ejectors located inside the magazines, one of the staple semibushes being fixed on a staple body and the other, on a staple strip locked in position with respect to said body, both of said semibushes being adapted, when brought together, to establish a staple member of the instrument having a cylindrical bore for the tubular organ to pass, said staple member being locked in position with respect to the supporting member of the instrument; said staple semibushes externally embracing said supporting semibushes in such a manner that an annular gap is defined between said staple semibushes and said supporting semibushes, said gap being intended for the walls of the tubular organ being sutured to accommodate, whereas provided on the outer cylindrical surface of the supporting semibushes are depressions for staples to bend, and radial slots are made in the staple semibishes, said slots being located opposite said respective depressions in the supporting semibushes; said slots accommodating traversably mounted magazines and ejectors, both said magazines and said ejectors having pivots arranged in curvilinear grooves which are provided in the staple and magazine semirings and are adapted to get in movable engagement therewith; a mechanical actuator adapted to impart motion to the magazine semirings, said actuator being made as a strip traversable with respect to the staple body and having one of its ends threaded in order to interact with a sliding nut, the other end of said strip being adapted to interact with a lug held to the magazine semiring of the staple semibush which is secured on the staple body; a mechanical actuator adapted to impart motion to the staple semirings, said actuator being made as an actuating lever involutely coupled with the staple semirings, according to the invention provision is made in the instrument involved for a means to prevent the staple semibushes from getting disjoined in the course of operation and to fix the position of the centre of the hole thereof with respect to the position of the centre of the hole of the supporting semibushes for the tubular organ to suture uniformly, whereas the magazines are so arranged as to be replaced after the operation, for which purpose the magazine semirings and the staple semirings have open-end curvilinear grooves and are detachable with respect to the staple semibushes, the outer walls of the latter having recesses for the magazines to reload, said recesses being arranged along the radius coinciding with the radius of the radial slots, provision being also made for an automatic restrictor of a radial synchronous movement of the magazines and the ejectors towards the centre.

Such a constructional arrangement of the surgical instrument enables one to attain a stable circumferential staple bending which provides for perfect tightness and reliability of the anastomosis established.

In addition, the means for preventing the staple semibush from getting disjoined in the course of operation and for fixing the centre of the hole thereof with respect to the centre of the hole of the supporting semibushes for the tubular organ to uniformly suture is essentially a hinge lock located on the outer surface of the staple semibushes and a detents located on the inner surface of the staple semibushes so as to interact with shanks provided on the outer surface of the supporting semibushes.

The above constructional feature provides for higher robustness of the instrument and reliable operation in the course of suturing.

It is expedient that the magazines carry one more row of U-shaped staples located under said row of staples, whose backs are square with the longitudinal axis of the supporting semibushes, the outer surface of each of said semibushes being made polyhedral, and one more row of depressions is provided on the faces of said polyhedral surface for staples to bend.

This is necessary to add to the tightness and reliability of anastomosis established.

It is also desirable that the automatic restrictor of a radial synchronous movement of the magazines and ejectors towards the centre be provided as a pivot positively locked on the strip of the mechanical actuator of the magazine semirings, said pivot passing through the staple body, and a shaped recess in the form resembling the letter P, located on the surface of the shorter arm of the actuating lever, said surface facing the staple body, while the narrower portion of said recess faces the hinge joint of the actuating lever and is bounded by a longitudinal slot whose axis coincides with the longitudinal axis of the staple body, whereas the wider portion of said recess is defined by two arcuate wells of different radii the centre of which coincides with the fulcrum of the actuating lever, by a first inclined wall conjugated with the longer-radius arcuate wall and with a first wall of the longitudinal slot, and by a second inclined wall conjugated with the longer-radius arcuate wall and with the shorter-radius arcuate wall which is conjugated with a second wall of the longitudinal slot so that interaction of the pivot with the first inclined wall provides for a radial synchronous travel of the magazines and the staple ejectors towards the centre and, after the tubular organ has been sutured, said interaction restricts the movement of the ejectors away from the centre, whereas the interaction of the pivot with the second inclined wall restricts the radial travel of the ejectors towards the centre at the moment of suturing the tubular organ, and when the pivot engages the longitudinal slot the actuating lever gets arrested so as to prevent its operation upon an accidental pressing of said lever before the moment of suturing the tubular organ.

Such a constructional arrangement of the automatic restrictor provides for a synchronous radial movement of the magazines and the ejectors when setting the suturing gap, limits the movement of the staple ejectors with respect to the magazines in the course of suturing, protects the magazines and the staple ejectors against damage during the suturing, and locks the actuating lever.

The other end of the pivot is expedient to carry the other end of the strip which is made as a lever articulated to said pivot at one of its ends, while the other (free) end of said lever is articulated to the lug on the magazine semiring, said lug being located within the zone restricted by a minimum effort applied to the lever while the magazines are moved radially away from the centre, and while these are being moved towards the centre.

The above feature contributes to reloading the magazines with staples.

It is likewise reasonable that the staple body and the staple strip have L-shaped detents adapted for the supporting member of the instrument to hold with respect to the staple member thereof.

Said detents add to the robustness of the construction and lock the supporting member of the instrument with respect to the staple member thereof.

It is desirable that the surgical instrument proposed herein be provided with an attachment to the staple body, said attachment comprising a strip having a means for its being fixed to the staple body, the operative end of said strip having a radial projection to the outer surface of which is positively locked the supporting semibush provided with two rows of depressions, a lever being movably mounted at the centre of said supporting semibush, one of the ends of said lever being shaped as a segment having curvilinear grooves on the inner surface thereof and fitted with a number of teeth on its outer surface adapted for an involute meshing with the actuating lever, whereas the other end of the lever is adapted for the staple semiring and the segment to return into the initial position after the suturing has been over.

The aforesaid attachment extends the functional capacities of the surgical instrument being claimed as enabling a linear suture to be applied.

Presented below is a detailed description of the specific embodiments thereof given by way of illustration with reference to the accompanying drawings, wherein:

FIG. 3 is a side elevation of a surgical instrument for suturing tubular organs with U-shaped staples, according to the invention;

FIG. 4 is a view of the staple member of a surgical instrument, according to the invention;

FIG. 5 is a section taken along the line V—V in FIG. 1;

FIG. 6 is a section taken through the magazine semirings, taken along the line VI—VI in FIG. 5;

FIG. 7 is a section through the staple semirings, taken along the line VII—VII in FIG. 5;

FIG. 8 is a view facing the arrow D in FIG. 1;

FIG. 9 illustrates the construction of the magazines and the staple ejectors;

FIG. 10 is a view facing the arrow E in FIG. 1;

FIG. 11 illustrates the staple member of the surgical instrument with a lever-actuated movement of the magazine semirings at the moment of reloading the instrument, according to the invention;

FIG. 12 shows a surgical instrument for suturing tubular organs with U-shaped staples, featuring L-shaped detents for locking the staple member of the instrument with respect to the supporting member thereof, having a lever-actuated movement of the magazine semirings, according to the invention;

FIG. 13 is a section taken along the line XIII—XIII in FIG. 12;

FIG. 14 is a side elevation of a surgical instrument of FIG. 12, according to the invention;

FIG. 15 is a section taken along the line XV—XV in FIG. 1;

FIG. 22 is a bottom view of an attachment to the staple body, according to the invention;

FIGS. 23, 24 show a side elevation of FIG. 22;

FIG. 25 is a plan view of FIG. 22;

FIG. 27 is a plan view of FIG. 26;

FIG. 29 is a bottom view of the attachment in assembly with the staple body, according to the invention.

Figure 1:
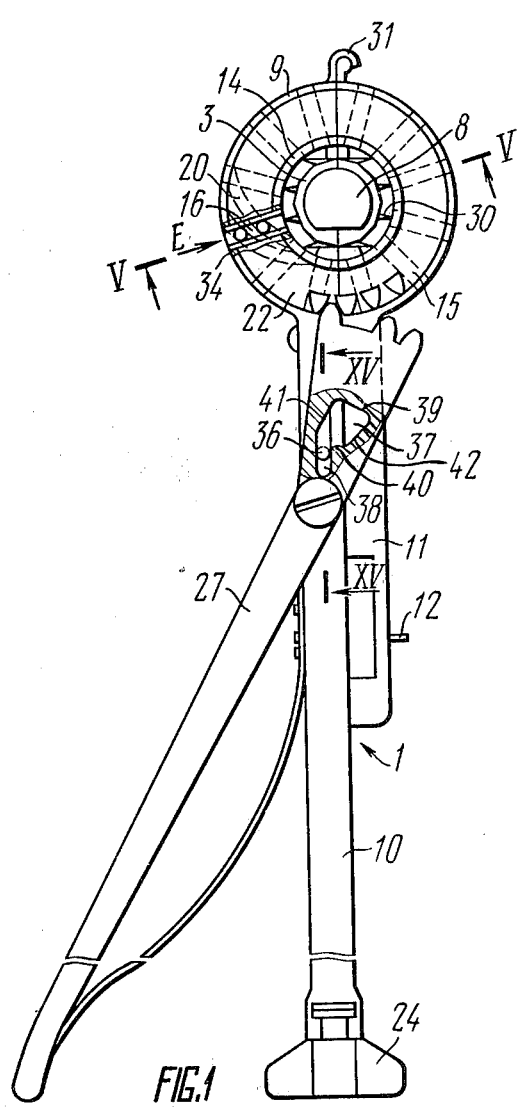
FIG. 1 is a diagrammatic plan view of a surgical instrument for suturing tubular organs with U-shaped staples, according to the invention.
Figure 2:
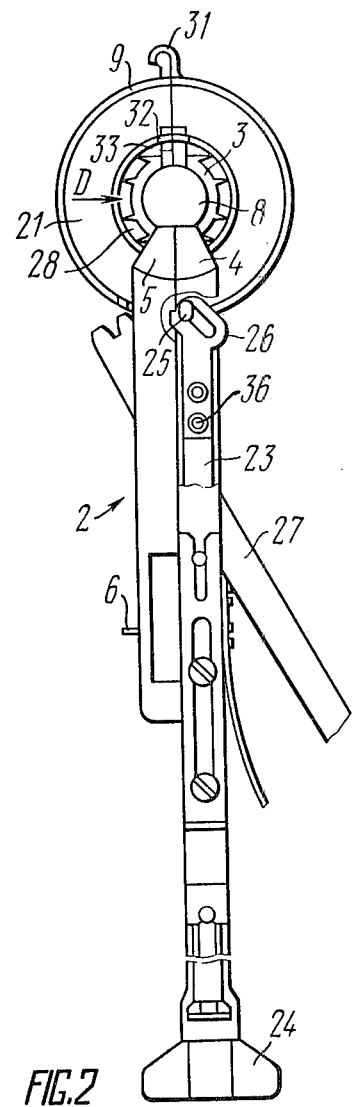
FIG. 2 is a bottom view of a surgical instrument for suturing tubular organs with U-shaped staples, according to the invention.

The herein-proposed surgical instrument is comprised of two members viz., a staple member 1 (FIG. 1) and a supporting member 2 (FIG. 2).

The supporting member 2 comprises two supporting semibushes 3 of which one is made fast on a supporting body 4, and the other, on a supporting strip 5. The supporting strip 5 is locked in position with respect to the supporting body 4 through a locking strip 6 which is adapted to get in engagement with a pivot 7 (FIG. 3) positively held to the supporting body 4. The supporting strip 5 and the supporting body 4 establish, when brought together, the supporting member 2 (FIG. 2) of the instrument, having a cylindrical bore 8 for the tubular organ to accommodate.

The staple member 1 (FIG. 1) of the instrument comprises two staple semibushes 9 of which one is made fast on a staple body 10, and the other, on a stable strip 11. The staple strip 11 is secured in position with respect to the staple body 10 through a locking strip 12 which is adapted to get in engagement with a pivot 13 (FIG. 3) positively held to the staple body 10. When brought together the staple strip 11 and the staple body 10 define the staple member 1 (FIG. 1) of the instrument, having a cylindrical bore 14 (FIG. 4) for the tubular organ to accommodate.

The staple semibushes 9 have radial slots 15 (FIG. 5) which accommodate movable mounted magazines 16 provided with pivots 17, and staple ejectors 18 provided with pivots 19. The pivots 17 and 19 are engaged with curvilinear grooves 20 (FIGS. 6, 7) made on the inner surfaces of magazine semirings 21 (FIG. 6) and staple semirings 22 (FIG. 7), respectively.

The mechanical actuator of the magazine semirings 21 (FIG. 6) is shaped as a strip 23 (FIG. 2) traversable with respect to the staple body 10 (FIG. 3), one of the ends of said strip being made threaded to engage sliding nut 24, whereas the other end of the strip 23 is shaped as a fork 26 (FIG. 4) adapted to interact with a lug 25 held to the magazine semiring 21 of the staple semibush 9 which is fastened to the staple body 10 (FIG. 3).

The mechanical actuator of the staple semirings 22 (FIG. 7) is made as an actuating lever 27 (FIG. 1) involutely coupled to the staple semirings 22.

The staple member 1 of the instrument is locked in position with respect to its supporting member 2 (FIG. 2) so that the staple semibushes 9 embrace externally the supporting semibushes 3 in such a manner that an annular gap is defined in between the staple semibushes 9 and the supporting semibushes 3, adapted for the walls of the tubular organ being sutured to accommodate. The outer cylindrical surface of the supporting semibushes 3 is provided with depressions 29 (FIG. 8) for staples to bend, and with spikes 30 for the tubular organ to be put thereon during operation.

In order to impart an adequately high robustness to the entire construction of the instrument and attain a high quality tightness of the tubular organ being sutured, the thoracic aorta inclusive, provision is made in the surgical instrument under consideration for a means to prevent the staple semibushes 9 (FIG. 4) from getting disjoined in the course of operation, and to fix the position of the centre of a cylindrical bore (hole) 14 with respect to the position of the centre of a cylindrical bore (hole) 8 (FIG. 2) of the supporting semibushes 3 so as to attain a uniform suturing of the tubular organ. Said means is essentially a hinge lock 31 provided on the outer surface of the staple semibushes 9, and detents 32 located on the inner surface of the staple semibushes 9 and adapted to interact with shanks 33 provided on the outer surface of the supporting semibushes 3. Each of the magazines 16 (FIG. 9) is so mounted as to be replaced after the operation. To this end the magazine semirings 21 (FIG. 6) and the staple semirings 22 (FIG. 7) have open-end curvilinear grooves 20 (FIGS. 6, 7) and are detachable with respect to the staple semibushes 9 (FIG. 1). The outer walls of the staple semibushes 9 have recesses 34 for the magazines 16 (FIG. 3) to reload, said recesses being arranged along the radius coinciding with the radius of the radial slots 15. The magazines 16 have each either one or two rows 35 (FIG. 9) of U-shaped staples (FIG. 9 representing an embodiment of the magazines 16 carrying two rows 35 of the staples), the backs of said staples being arranged square with the longitudinal axis of the supporting semibushes (FIG. 5). The outer surface of the supporting semibushes 3 is made polyhedral, the faces of said surfaces having either one or two rows of the depressions 29 (FIG. 8) for staples to bend (FIG. 8 illustrating an embodiment of said polyhedral surface of the supporting semibushes 3 provided with two rows of the depressions 29).

To provide a synchronous radial movement of each of the magazines 16 (FIG. 9) and of the staple ejector 18 when selecting the suturing gap, and to restrict the travel of the staple ejector 18 with respect to the magazine 16 in the course of suturing, provision is made in the herein-proposed instrument for an automatic restrictor of a synchronous radial movement of the magazines 16 and the staple ejectors 18 towards the centre. Said automatic restrictor is in effect a pivot 36 (FIG. 2) positively locked on the strip 23 of the mechanical actuator of the magazine semirings 21 and passing through the staple body 10 (FIG. 1), and a shaped recess 37 in the form resembling the letter P, located on the surface of the shorter arm of the actuating lever 27, said surface facing the staple body 10. The narrower portion of the shaped recess 37 faces the hinge joint of the actuating lever 27 and is bounded by a longitudinal slot 38 whose axis coincides with the longitudinal axis of the staple body 10. The wider portion of the shaped recess 37 is defined by two arcuate walls 39, 40 of different radii, the centre of which coincides with the fulcrum of the actuating lever 27, and by two inclined walls 41, 42. The former inclined wall 41 is conjugated with the longer-radius arcuate wall 39 and with the first wall of the longitudinal slot 38, whereas the latter inclined wall 42 is conjugated with the arcuate wall 40 which is conjugated with the second wall of the longitudinal slot 38.

Interaction of the pivot 36 with the former inclined wall 41 provides for a synchronous radial movement of the magazines 16 (FIG. 5) and the staple ejectors 18 towards the centre, and after the tubular organ has been sutured, said interaction restricts the movement of the staple ejectors 18 away from the centre. Interaction of the pivot 36 (FIG. 1) with the latter inclined wall 42 restricts the radial movement of the staple ejectors 18 (FIG. 5) towards the centre at the moment of suturing the tubular organ. When the pivot 36 (FIG. 1) engages the longitudinal slot 38 the actuating lever 27 gets arrested to prevent its operation upon an accidental pressing of said lever before the moment of suturing the tubular organ.

The herein-proposed surgical instrument operates as follows. Before suturing tubular organs the instrument must be charged with the replaceable magazines 16 (FIG. 9) preliminarily loaded with U-shaped staples. Then one must rotate the sliding nut 24 (FIG. 2) counterclockwise to disengage the fork 26 from the lug 25, and shift the lug 25 manually clockwise till meeting a stop 43 (FIG. 4). Next the magazines 16 (FIG. 4) are inserted into the circumferentially arranged recesses 34 (FIGS. 3, 10) of the staple semibushes 9 (FIG. 3). At the same time th pivots 17 (FIG. 9) of the magazines 16 engage the curvilinear grooves 20 (FIG. 6). Thereupon the lug 25 (FIG. 2) is manually returned into the initial position, rotating it counterclockwise. As a result of the movement performed by the magazine semirings 21 (FIG. 6) and the interaction of the pivots 17 with the curvilinear grooves 20 all the magazines 16 travel radially towards the centre, and their outside edge coincides with the outside edge of the staple semibushes 9. After that one must rotate the sliding nut 24 (FIG. 2) clockwise to return the fork 26 into the initial position till it engages the lug 25. This done, the instrument is ready for operation. Then the supporting strip 5 is disengaged from the supporting body 4 by shifting the locking strip 6 till it thrusts against the pivot 7 (FIG. 3). Proceeding in a similar way one must disengage the staple strip 11 from the staple body 10 by manipulating the locking strip 12.

One of the ends of the tubular organ being sutured is embraced externally by the supporting semibushes 3 (FIG. 2). Then the vessel end is put on the spikes 30 on the side of the tunica extima, whereupon the other vessel end is put on the same spikes on the side of the tunica intima. Next the staple body 10 (FIG. 3) is introduced into the wound, its staple semibush 9 is brought under the vessel and is joined with the supporting body 4 through the pivots 44, 45, the locking strip 46 and the detent 32 (FIG. 2). After that there is introduced into the wound the staple strip 11 (FIG. 1) carrying its staple semibush 9. Then the hinge lock 31 is engaged and the staple strip 11 is forced against the staple body 10 and locked with the locking strip 12. Thus the instrument is completely assembled on the vessel to be sutured. Further on one must adjust the suturing gap, for which purpose the sliding nut 24 is rotated and the fork 26 (FIG. 2) is shifted towards the centre. As result the lug 25, while sliding on the inner surfaces of the fork 26, is displaced along with the magazine semirings 21 counterclockwise, which urges all the magazines 16 (FIG. 5) to travel radially towards the centre till approximating the vessel cuff as close as not to overcompress it. The movement of the strip 23 (FIG. 2) and the fork 26 during selection of the suturing gap causes the pivot 36 to move as well. While moving the pivot 36 exerts upon the first inclined wall 41 (FIG. 1) of the shaped recess 37 so as to shift the actuating lever 27 which, in turn, sets in motion the staple semirings 22. As a result, the curvilinear grooves 20 (FIG. 7) in the staple semirings 22 get in engagement with the pivots 19 of the staple ejectors 18 (FIG. 9) to actuate the ejectors 18 to move after the magazines 16. Then the actuating lever 27 (FIG. 2) is pressed, and movement is imparted through the involute meshing to the staple semirings 22, which sets in motion all the ejectors 18 (FIG. 5). The ejectors expel the staples from the magazines 16, the staple legs, after having pricked the vessel cuff, catch the depressions 29 (FIG. 8) in the supporting semibushes (FIG. 5) to get bent into the shape of the letter B, thus uniting the vessel ends. The pivot 36 (FIG. 1) thrusts against the second inclined wall 42 of the shaped recess 37 as a result of pressing the actuating lever 27, thus restricting the motion of the ejectors 18 (FIG. 5) to suit the travelling of the magazines 16. The inclined walls 41 and 42 (FIG. 1) are so designed that when selecting the suturing gap the outside edge of the ejector 18 (FIG. 9) is at the level of the outside edge of the magazine 16, and when suturing the inside edge of the ejectors 18 does not project beyond the inside edge of the magazine 16. Suturing over, the magazines 16 (FIG. 4) are returned into the initial position by rotating the sliding nut 24 (FIG. 1) counterclockwise, the instrument is removed from the sutured vessel in a reverse sequence of operations. The vessel is put off the spikes 30 (FIG. 8) by rotary motion of the supporting semibushes 3 (FIG. 2). Thus, the vessel is sutured. As a rule, the time required for an anastomosis to establish does not exceed 1 to 2 minutes.

In order to recharge the instrument first one must join the staple strip 11 (FIG. 4) with the staple body 10. Then one must rotate the sliding nut 24 (FIG. 2) so as to disengage the fork 26 from the lug 25. The lug 25 is to be turned clockwise manually till it meets the stop 43. As a result, the used-up magazines 16 (FIGS. 6, 7) come off the curvilinear grooves 20 (FIGS. 6, 7) through the recesses 34 (FIG. 4), whereupon they are easily removed by hand or through pincers. To provide convenience in catching the magazines 16 slots 47 are provided on the lateral surfaces thereof. The used-up magazines 16 removed, the fresh plastics or metallic magazines 16 (FIG. 4) preliminarily loaded with staples are inserted into the same recesses 34 (FIG. 3). The magazine charging procedure has been described hereinbefore.

With a view to providing an automatic resetting of the magazine semirings 21 into the initial position in order to remove the used-up magazines 16 from the instrument, FIG. 11 illustrates an embodiment of the mechanical actuator of the magazine semirings 21, wherein the end of the strip 23 (FIG. 2) adapted to interact with the lug 25 made fast on the magazine semiring 21 of the staple semibush 9 locked in position on the staple body 10 (FIG. 11), is shaped as a lever 48. One of the ends of the lever 48 is articulated to the pivot 36, and the other (vacant) end of the lever 48 is articulated to the lug 25 located on the magazine semiring 21 within the zone restricted by a minimum effort applied to the lever 48 while the magazines 16 are being moved radially away from the centre or towards the centre.

FIG. 13 represents an embodiment of the means for locking the staple member 1 (FIG. 1) with respect to the supporting member 2 (FIG. 2) so as to add to the robustness of the construction of the instrument and better the operating conditions for the surgeon. The supporting member 2 is locked with respect to the staple member 1 (FIG. 1) by virtue of L-shaped detents 49 (FIGS. 12, 13) held in place on the staple strip 11 (FIG. 14) and on the staple body 10. For a more rigid fastening of the staple strip 11 to the staple body 10, and of the supporting strip 5 (FIG. 12) to the supporting body 4, the shaped pivots 13 (FIG. 14) and 7 are relocated to the bottom edge of the staple strip 11 and of the supporting strip 5, whereas the locking strips 12 and 6 are turned through 180°, and the locking strip 46 (FIG. 3) with the pivot 44 is dispensed with. A through slot 50 (FIG. 14) is provided on the side surface of the staple body 10 (FIG. 14) that accommodates the strip 23, said slot giving access to the side surface of the strip 23 with an indexing projection 51, while on the surface of the staple body 10 there are provided marks designated as follows: "A"—minimal gap for washing; "B"—the actuating lever 27 (FIG. 12) is locked; "C" (FIG. 14)—instrument recharging. Located between the marks "A" and "B" is the suturing gap setting scale graduated in millimeters. The above scale helps the surgeon select a predetermined suturing gap and set the index 51, by meand of the sliding nut 24, to any desired position wherein either recharging of the instrument with the replaceable magazines 16 (FIG. 9) or its disassembly occurs.

The operation of the instrument incorporating the aforesaid constructional features occurs as follows.

Prior to suturing the ends of vessels or of some other tubular organs, such as intestines, the esophagus, etc., the instrument must be charged with the replaceable magazines 16. To this end the supporting member 2 (FIG. 12) of the instrument must be disengaged from the staple member 1 (FIG. 11) thereof proceeding as follows. The locking strip 12 (FIG. 14) is moved all the way up to disengage it from the pivot 13. Then the bottom end of the staple strip 11 is to be raised, while its top end still engages the hinge joint 31. The staple strip 11 is removed by being moved down, with the result that the supporting member 2 (FIG. 12) of the instrument is released from the left-hand detents 32 and the left-hand L-shaped detents 49. Then the supporting member 2 of the instrument is raised a little through a small angle till it disengages from the right-hand detents 32 and the right-hand L-shaped detents 49, and from the pivot 45 (FIG. 14). Upon removing the supporting member 2 (FIG. 12) of the instrument the staple strip 11 (FIG. 14) is reset to the initial position. The sliding nut 24 is rotated counterclockwise to bring the index 51 of the scale with the mark "C" (instrument recharging). As a result, the strip 23 and the lever 48 are shifted downwards to set in motion the magazine semirings 21 (FIG. 11). If some used-up magazines 16 remain in the instrument the curvilinear grooves 20 (FIG. 6) will displace the pivots 17 of the magazines 16 (FIG. 11) by virtue of the rotary motion of the magazine semirings 21, and the magazines 16 themselves as far outwards as possible. As a result, the outer ends of the curvilinear grooves 20 (FIG. 6) approximate the recesses 34. The pivots 19 (FIG. 9) of the ejectors 18 are free to come off the outside recesses 34 (FIG. 7) of the staple semibushes 9 (FIG. 11). Then the used-up magazines 16 are removed by hand or through pincers, and the fresh magazines are inserted into the outside recesses 34 (FIG. 14) of the staple semibushes 9 instead. The sliding nut 24 is rotated clockwise to displace the strip 23 along with the lever 48 till the index 51 of the scale coincides with the mark "B" (locked). As a result, the curvilinear grooves 20 (FIG. 6) of the magazine semirings 21 shift the pivots 17 of the magazines 16 (FIG. 11) and hence the magazines themselves radially towards the centre. Upon finally plunging the magazines 16 into the staple semibushes 9 of the instrument, the pivots 19 (FIG. 7) of the ejectors 18 (FIG. 9) engage the curvilinear grooves 20 (FIG. 7) of the staple semirings 22. By that instance the actuating lever 27 (FIG. 12) is arrested, and this terminates the instrument recharging procedure. The above procedure takes 1 to 1.5 minutes to occur. The instrument cannot be recharged when assembled due to the provision of a blocking projection 52 on the supporting body 4 (FIG. 14), against which the bottom end of the lever 48 (FIG. 14) thrusts, thus rendering the counterclockwise rotation of the sliding nut 24 impossible. This prevents the magazines 16 (FIG. 11) against being extended from the staple semibushes 9 outwards and thus accidental falling down into the operative wound.

Considered below are the techniques of suturing blood vessels or other hollow tubular organs by the end-to-end and end-to-side methods, as well as suturing circular patches in the case of lateral defect of these organs.

Before suturing the charged instrument is taken to its four major pieces. To this the locking strip 12 (FIG. 14) is released and the staple strip 11 is removed, whereupon the supporting member 2 (FIG. 12) of the instrument is disengaged from the supporting body 10 (FIG. 14). The supporting member 2 (FIG. 12) is taken to two pieces, viz., the supporting strip 5 is disengaged from the supporting body 4 by virtue of the movement performed by the locking strip 6.

Figure 16:
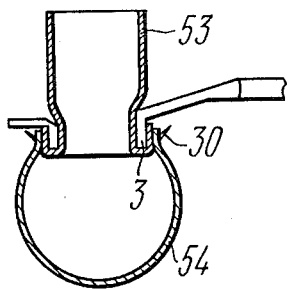
FIGS. 16, 17, 18 illustrate schematically the vascular suture by the end-to-side method.
Figure 19:
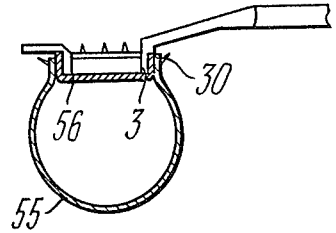
FIGS. 19, 20, 21 illustrate schematically the suturing of a circular patch into a lateral defect of a tubular organ.
Figure 17:
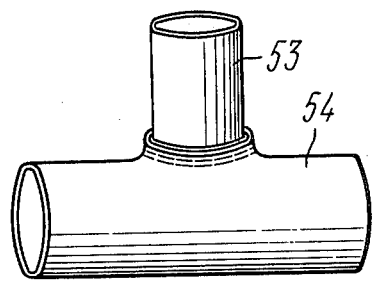
Figure 20:
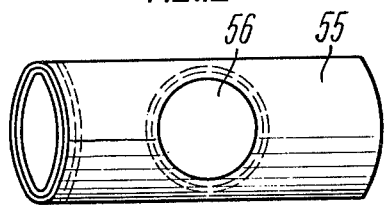
Figure 18:
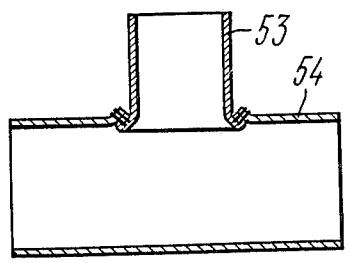
Figure 21:
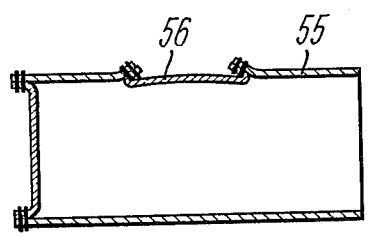

The supporting semibush 3 located in the supporting body 4, is brought under one of the ends of the vessel being sutured. The vessel is covered by the supporting semibush 3 located on the supporting strip 5, whereupon the locking strip 6 is closed. The vessel free end 5 mm long is left above the supporting semibushes 5 of the instrument. The margins of the vessel free end are uniformly put on the spikes 30 (FIGS. 16, 17, 18) of the supporting semibushes 3 on the side of the tunica extima, using pincers. Then the vessel everted on the supporting semibushes 3 on the side of the tunica extima, using pincers. Then the vessel everted on the supporting semibushes 3 and fixed on the spikes 30 is introduced into the lumen of the other vessel end and its margins are fixed on the same spikes 30. In the case of the end-to-side anastomosis, a circular hole is to be excised in the lateral surface of the other vessel 54 to be sutured, or a longitudinal incision is made so that the supporting semibushes 3 of the instrument carrying the vessel 53 everted thereon should enter the vessel lumen under some effort. Then the margins of the vessel 54 having a lateral defect, are put on the same spikes 30 on the side of the tunica intima. When suturing a circular patch in the case of a lateral defect of a tubular organ 55 (FIGS. 19, 20, 21), a circular allotransplant or exilantat 56 is placed onto the supporting semibushes 3 from above, with its inner surface facing outwards, and its margins are put on the spikes 30. Then the supporting semibushes 3 whose bore is closed by the transplant 56, are introduced into the lateral defect of the tubular organ 55 the margins of which is put on the same spikes 30 on the side of the tunica intima. Further technique applied to suturing a patch does not differ end-to-end and end-to-side suturing of tubular organs,.

Upon fixing the organs being sutured on the spikes 30 of the supporting semibushes 3 the staple semibush 9 (FIG. 14) is introduced into the wound, which has preliminarily been held to the staple body 10, whereupon the staple semibush is joined first with the slot 57 (FIG. 12) through the pivot 45, then with the detents 32 through the shanks 33 and the L-shaped detents 49, so as to embrace the supporting body 4. Then introduced into the wound is the staple strip 11 (FIG. 14), said strip is engaged with the lock joint 31 and the strip 12 is locked. This terminates the assembly of the instrument in the operative wound. Then the sliding nut 24 is rotated clockwise to actuate the magazine semirings 21 (FIG. 11) which, in turn sets in radial motion towards the centre all the magazines 16, whereas the ejectors 18 (FIG. 9) are being moved radially towards the centre in synchronism with the magazines 16. This is effected due to an automatic movement of the actuating lever 27 (FIG. 1) under the action of the pivot 36 and due to the presence exerted by said pivot upon the inclined wall 41 of the shaped recess 37, which actuates the staple semirings 22 (FIG. 7) with the curvilinear grooves 20.

The actuating lever 27 (FIG. 1) is pressed till the inclined wall 42 of the shaped recess 37 meets the pivot 36 to actuate the staple semirings 22 which, in turn, shift the ejectors 18 (FIG. 9). The latter expel U-shaped staples from the magazines 16. The staple legs pierce the vessel cuff and get into the depressions 29 (FIG. 8) in the supporting semibushes 3 (FIG. 5) to be bent into the shape of the letter B, thus reliably uniting the ends of the tubular organs being sutured. Thereupon the sliding nut 24 (FIG. 14) is rotated counterclockwise till the mark "B" on the scale so as to return the magazines 16 (FIG. 9) along with the ejectors 18 into the initial position.

Then the instrument is disassembled by reversing the assembly procedure, and the vessel cuff is released from the spikes 30 (FIG. 5) by rotating the supporting semibushes 3 in the opposite directions.

To establish an end-to-end anastomosis takes 2 to 3 minutes, and end-to-side anastomosis or to suture a vascular patch, 3 to 5 minutes. A double-row mechanical suture provides for perfect tightness of the anastomoses thus established. By loading the magazines 16 (FIG. 9) with staples arranged in different ways for different operations one can obtain a single-row, double-row, Z-shaped, slant, cross-shaped, and some other sutures.

To supply a linear structure to most diverse organs, such as the root of the lung, blood vessels, the bronchi, the esophagus, the intestines, etc. the proposed surgical instrument, particularly, the staple body 10 (FIG. 14) thereof is provided with an attachment 58 (FIG. 22).

Said attachment 58 (FIG. 18) to the staple body 10 (FIG. 14) comprises a strip 59 (FIGS. 22 through 25), the effective end 60 of said strip having a radial projection 61. The supporting semibush 3 is positively locked to the outer surface of the radial projection 61. The outer surface of the supporting semibush 3 is made polyhedral, the faces thereof having two rows of the depressions 29.

Figure 28:
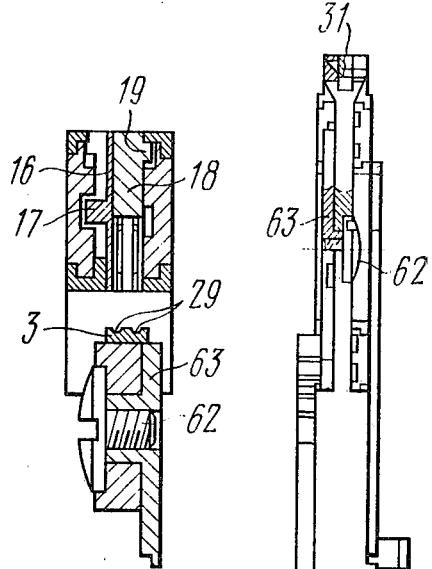
FIG. 28 is a section taken along the line XXVIII—XXVIII in FIG. 27.
Figure 26:
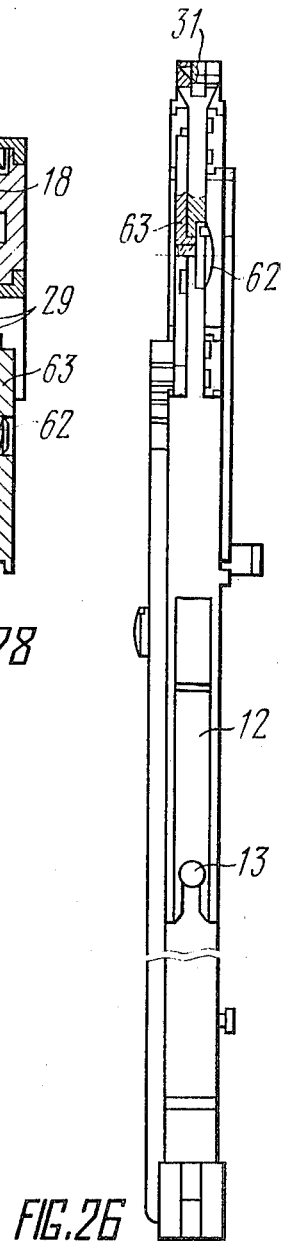
FIG. 26 is a side elevation of the attachment in assembly with the staple body.

A lever 64 (FIG. 25) is articulately mounted at the centre of the supporting semibush 3 by means of a pivot made as a screw 62 (FIGS. 26, 28) and a bushing 63. One of the ends of the lever 64 is shaped as a segment 65. The inner surface of the segment 65 has the curvilinear grooves 20, while the outer surface thereof carries a number of teeth adapted for an involute meshing with the actuating lever 27 (FIG. 27) of the instrument. The other end of the lever 64 is adapted for the staple semiring 22 and the segment 65 to return to the initial position after the suturing is over.

Figure 30:
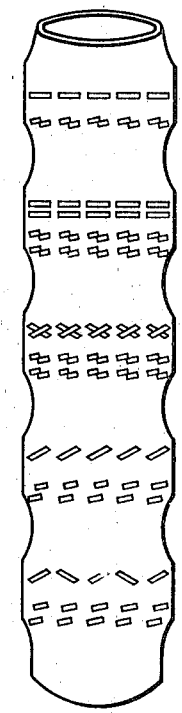
FIG. 30 illustrates various types of linear sutures applied by the surgical instrument, according to the invention.

The instrument provided with the attachment 58 to the staple body 10 operates as follows. Prior to suturing up the stump of one organ or the other the instrument is charged with the magazines 16 (FIG. 9) preliminarily loaded with U-shaped staples, the charging procedure being similar to that described hereinbefore. Then the attachment 58 (FIG. 21) is disengaged from the staple body 10 by shifting the locking strip 12 upwards so as to disengage the locking strip 12 from the pivot 15 (FIG. 14). The free end of the strip 59 (FIG. 29) is moved away from the staple body 10 (FIG. 27) till its disengagement from the pivot 13 (FIG. 14), with the result that the operative end 60 (FIG. 29) of the strip 59 performs rotary motion round the hook of the hinge lock 31. Then the attachment 58 is moved down at an angle to disengage it from the staple body 10 (FIG. 27). The staple semibush 9 is brought under the organ to be sutured, and said organ is covered by the attachment 58, for which purpose the latter is joined with the staple body 10 through the hinge lock 31, the pivot 13 (FIG. 14) and the locking strip 12. The sliding nut 24 (FIG. 29) is rotated clockwise to adjust the suturing gap, with the result that the strip 23 with the lever 48 moves up, thus displacing the lug 25 and the magazine semiring counterclockwise, which brings the curvilinear grooves 20 into engagement with the pivots 17 of the magazines 16 (FIG. 27) and urges all the magazines 16 to move radially towards the centre. The organ being sutured confined between the supporting semibush 3 (FIG. 29) and the inner edge of the staple semibush 9, is moderately compressed by the magazines 16 (FIG. 27) extended inwards. Thereupon, the actuating lever 27 is pressed to actuate the staple semiring 22 and the segment 65 which, in turn, brings the curvilinear grooves 20 (FIG. 23) into engagement with the pivots 19 (FIG. 27) of the ejectors 19 (FIG. 9) and urges all the ejectors 18 to traverse radially towards the centre. This, in turn, expels the staples from the magazines 16. The staple legs pierce the tissue and get into the depressions 29 (FIG. 23) in the supporting semibush 3 to be bent into the shape of the letter B. Then, remaining the instrument on the organ being sutured one must excise the unnecessary portion of the organ (e.g., the pulmonary lobe) with a scalpel along the lateral edge of the staple semibush 9. Then the sliding nut 24 (FIG. 27) is rotated all the way counterclockwise to return the magazines 16 into the initial position, and the attachment 58 is removed. Experimental studies have shown that the thus-formed stump of the organ needs no additional hemostatic measures. By way of combining the attachment 58 with the staple body 10 one can stitch up the stump of an organ with a single-row, double-row, cross-shaped, slant, Z-shaped, or any other mechanical suture which have not heretofore been known in the art (FIG. 30). All the types of sutures are obtained by various modes of loading U-shaped staples into the slots of the magazines 16 (FIG. 9), without changing the supporting semibush 3 (FIG. 22). To take an example a cross-shaped suture can be obtained by inserting the staples into the slots of the magazines 16 (FIG. 9) in a criss-cross way. In other words, the name of a suture corresponds to the position of staples in the magazines 16.

What is claimed is:

1. A surgical instrument for suturing tubular organs with U-shaped staples, comprising:
   a supporting body;
   a supporting strip fixed in position with respect to said supporting body;
   two supporting semibushes;
   a first of said supporting semibushes made fast with one of its ends on said supporting body;
   a second of said supporting semibushes made fast with one of its ends on said supporting strip and establishing, when brought together with said first supporting semibush, the supporting member of the instrument having a cylindrical bore for the tubular organ to pass;
   a staple body;
   a staple strip locked in position with respect to said staple body;
   two staple semibushes;
   a first of said staple semibushes made fast with one of its ends on said staple body and externally embracing said first supporting semibush;
   a second of said staple semibushes made fast with one of its ends on said staple strip and externally embracing said second supporting semibush, and adapted to establish, when brought together with said first staple semibush, the staple member of the instrument having a cylindrical bore for the tubular organ to pass;
   an annular gap adapted for accommodating the walls of the tubular organ being sutured, said gap being established by said staple semibushes when the latter embrace said supporting semibushes;
   staples;
   depressions for said staples to bend, said depressions being situated on the outer cylindrical surface of said supporting semibushes;
   a means for preventing said staple semibushes from being disjoined during the operation and for fixing the position of the centre of the hole thereof with respect to the position of the centre of the hole of said supporting semibushes so as to attain a uniform suturing of the tubular organ being handled;
   radial slots in said staple semibushes, arranged opposite said respective depressions on said supporting semibushes;
   magazine semirings mounted detachably with respect to said staple semibushes;
   staple semirings mounted detachably with respect to said staple semibushes;
   magazines mounted movably in said radial slots of said staple semibushes so as to be replaced after the operation;
   ejectors for said staples to push out, said ejectors being accommodated inside said magazines;
   curvilinear grooves in said magazine semirings, said grooves being open-end ones for said magazines to be mounted with a possibility of being replaced after the operation;
   curvilinear grooves in said staple semirings, said grooves being open-end ones for said staple ejectors to accommodate;
   pivots of said magazines, arranged in said curvilinear grooves of said magazine semirings and adapted to engage movably said grooves;
   pivots of said staple ejectors, arranged in said curvilinear grooves of said staple semirings so as to movably engage said grooves;
   recesses for said magazines to reload, said recesses being made on the outer walls of said staple semibushes and arranged along the radius coinciding with the radius of said radial slots;

an automatic restrictor of a synchronous movement of said magazines and said ejectors in a radial direction towards the centre;

a mechanical actuator for said magazine semirings to traverse;

a lug of said mechanical actuator of said magazine semirings, made fast on said magazine semiring of said first staple semibush;

a strip of said mechanical actuator of said magazine semirings, said strip being traversable with respect to said staple body, the first end of said strip being threaded, while the second end is adapted to interact with said lug;

a sliding nut of said mechanical actuator of said magazine semirings, said nut being fitted on the threaded end of said strip;

a mechanical actuator for said staple semirings to traverse;

a double-arm actuating lever of said mechanical actuator of said staple semirings, said lever being engaged involutely with said staple semirings.

2. A surgical instrument as claimed in claim 1, wherein said means for preventing said staple semibushes from being disjoined during the operation and for fixing the position of the centre of the hole thereof with respect to the position of the centre of the hole of said supporting semibushes for the tubular organ to suture uniformly, comprises:

a hinge lock of said means, provided on the outer surface of said staple semibushes so as to prevent these from being disjoined during the operation;

shanks of said means, each of them being located on the outer surface of the vacant end of each of said supporting semibushes;

detents of said means, situated on the inner surface of the vacant end of each of said staple semibushes and adapted to interact with said shanks so as to fix the position of the centre of the hole of said staple semibushes with respect to the position of the centre of the hole of said supporting semibushes for the tubular organ to suture uniformly.

3. A surgical instrument as claimed in claim 1, comprising:

one more row of U-shaped staples located in said magazines under said staples, the backs of said staples of the other row being square with the longitudinal axis of said supporting semibushes;

the surface of said supporting semibushes being a polyhedral one;

one more row of said depressions for said staples to bend, said depressions being made on the faces of said polyhedral surface of said supporting semibushes.

4. A surgical instrument as claimed in claim 1, wherein said automatic restrictor of a synchronous radial movement of said magazines and said ejectors towards the centre comprises:

a shaped recess in said automatic restrictor, in the form resembling the letter P, said recess being situated on the surface of the shorter arm of said actuating lever, facing said staple body, while the narrower portion of said recess faces the hinge hoint of said actuating lever and is bounded by a longitudinal slot whose axis coincides with the longitudinal axis of said staple body, whereas the wider portion of said recess is defined by two arcuate walls of different radii, the centre of which coincides with the fulcrum of said actuating lever, by a first inclined wall conjugated with the larger-radius arcuate wall and with a first wall of the longitudinal slot, and by a second inclined wall conjugated with the larger-radius arcuate wall and with the smaller-radius arcuate wall which is conjugated with a second wall of the longitudinal slot;

a pivot of said automatic restrictor, positively locked to said strip of said mechanical actuator of said magazine semirings, said pivot passing through said staple body so that interaction of said pivot with the first inclined wall of said shaped recess provides for a synchronous radial travel of said magazines and said ejectors towards the centre, and after the tubular organ has been sutured, said interaction restricts the movement of said ejectors away from the centre, whereas the interaction of said pivot with the second inclined wall of said shaped recess restricts the radial travel of said ejectors towards the centre at the moment of suturing the tubular organ, and when said pivot engages the longitudinal slot of said shaped recess said actuating lever gets arrested which prevents its operation upon an accidental pressing of said lever before the moment of suturing the tubular organ.

5. A surgical instrument as claimed in claim 4, wherein the other end of said strip is articulated at the other end of said pivot of said automatic restrictor, said other end of the strip being made as a lever whose vacant end is articulated to said lug on said magazine semiring, said lug being situated within the zone restricted by a minimum effort applied to said lever while said magazines are being moved radially away from the centre, and while these are being moved radially towards the centre.

6. A surgical instrument as claimed in claim 4, comprising L-shaped detents positively locked on said staple body and on said staple strip and adapted for holding the supporting member of the instrument with respect to the staple member thereof.

7. An attachment to said staple body of a surgical instrument, comprising:

a strip;

a means for holding said strip to said staple body;

an operative end of said strip having a radial projection to the outer surface of which said supporting semibush is positively locked, provided with two rows of said depression;

a pivot;

a lever movably mounted on said pivot at the centre of said supporting semibush at the supporting operative end of said strip;

a first end of said lever shaped as a segment having on its inner surface said curvilinear grooves, and on its outer surface, a number of teeth for an involute meshing with said actuating lever;

a second end of said lever adapted for said staple semiring and said segment to return into the initial position after the suturing has been over.

* * * * *